United States Patent
Luken

(10) Patent No.: US 9,470,669 B2
(45) Date of Patent: Oct. 18, 2016

(54) SYSTEM AND METHOD FOR FLEXIBLE FUEL ETHANOL CONCENTRATION AND HARDWARE MALFUNCTION DETECTION

(71) Applicant: Honda Motor Co., Ltd., Tokyo (JP)

(72) Inventor: Todd Luken, Utsunomiya (JP)

(73) Assignee: Honda Motor Co., Ltd., Tokyo (JP)

( * ) Notice: Subject to any disclaimer, the term of this patent is extended or adjusted under 35 U.S.C. 154(b) by 450 days.

(21) Appl. No.: 14/102,559

(22) Filed: Dec. 11, 2013

(65) Prior Publication Data

US 2015/0160174 A1   Jun. 11, 2015

(51) Int. Cl.
  *G01N 33/00*   (2006.01)
  *F01N 11/00*   (2006.01)
  *G01M 15/10*   (2006.01)
  *F02D 41/14*   (2006.01)

(52) U.S. Cl.
  CPC ........... *G01N 33/0004* (2013.01); *F01N 11/00* (2013.01); *G01M 15/102* (2013.01); *F02D 41/1495* (2013.01)

(58) Field of Classification Search
  CPC ............. G01N 33/0004; F01N 11/00; G01M 15/102; F02D 41/1495
  USPC ............................ 73/23.32, 114.01–114.76
  See application file for complete search history.

(56) References Cited

U.S. PATENT DOCUMENTS

| | | | |
|---|---|---|---|
| 6,016,796 A | 1/2000 | Dalton | |
| 6,397,583 B1 | 6/2002 | Davey et al. | |
| 6,714,856 B2 * | 3/2004 | Huff | G01N 33/2852 123/1 A |
| 6,901,741 B2 * | 6/2005 | Kobayashi | F01N 3/101 123/198 F |
| 7,103,467 B2 * | 9/2006 | Takahashi | F02D 41/1454 123/691 |
| 7,159,623 B1 | 1/2007 | Carr et al. | |
| 7,729,846 B2 | 6/2010 | Kitada et al. | |
| 7,865,295 B2 | 1/2011 | Tahima | |
| 8,965,662 B2 * | 2/2015 | Aoki | F02D 41/1495 701/103 |
| 2008/0196490 A1 * | 8/2008 | Fukagai | F02D 41/1456 73/114.72 |
| 2009/0314071 A1 | 12/2009 | Mukai | |
| 2010/0206059 A1 * | 8/2010 | Suzuki | F02D 19/0628 73/114.38 |

* cited by examiner

*Primary Examiner* — Hezron E Williams
*Assistant Examiner* — Marrit Eyassu
(74) *Attorney, Agent, or Firm* — Rankin, Hill & Clark LLP

(57) ABSTRACT

A system and method for flexible fuel ethanol concentration and hardware malfunction detection compares a current hardware reference value learned based on an air-fuel ratio detected during a pre-fuel mix period with a previous hardware reference value from a previous vehicle driving cycle, and detects a hardware malfunction when a difference between current and previous hardware reference values exceeds a predetermined threshold. The system and method also monitors the air-fuel ratio during a post-fuel mix period, and detects a hardware malfunction when the air-fuel ratio changes by more than a predetermined threshold during the post-fuel mix period. The system and method also compares an observed slope of the air-fuel ratio detected during a fuel mixing period over an amount of fuel consumed with an expected slope when a cold-start is detected, and detects a hardware malfunction when a difference between observed and expected slopes exceeds a predetermined threshold.

14 Claims, 7 Drawing Sheets

SYSTEM AND METHOD FOR FLEXIBLE FUEL ETHANOL CONCENTRATION AND HARDWARE MALFUNCTION DETECTION

BACKGROUND

The present disclosure generally relates to a system and method for determining a flexible fuel ethanol concentration, and more particularly relates to a system and method for distinguishing a change in flexible fuel ethanol concentration from a hardware malfunction.

Flexible fuel vehicles are able to run on mixtures of gasoline and ethanol. As the properties of the flexible fuel may vary from one refueling to the next, engine control software of the flexible fuel vehicle needs to learn the properties of the flexible fuel in the vehicle so as to optimally control operation of a vehicle engine. One example of a potentially variable flexible fuel property relates to an ethanol concentration of the flexible fuel. Specifically, different flexible fuel sources may provide flexible fuel having different ethanol concentrations. Therefore, the vehicle engine control software preferably learns the ethanol concentration of flexible fuel in a vehicle fuel tank so as to accordingly control vehicle fuel injection.

To detect ethanol concentration of a flexible fuel, modern flexible fuel vehicles typically do not use ethanol sensors. Rather, modern flexible fuel vehicles rely on air-fuel sensors to provide air-fuel feedback, which is used to estimate the ethanol concentration of the flexible fuel in the vehicle fuel tank based on changes in a stoichiometric air-fuel ratio. However, air-fuel feedback offsets caused by changes in ethanol concentration may not be distinguishable from offsets caused by hardware variation or malfunction. In markets having on-board diagnostic regulatory requirements for fuel metering malfunctions, such as those set forth by the California Air Resources Board, this may pose both an operational and a regulatory problem.

SUMMARY

According to one aspect, a method for determining a flexible fuel ethanol concentration and detecting a hardware malfunction is provided. The method includes detecting whether a refuel event has occurred, and when occurrence of the refuel event is detected, performing a primary ethanol concentration and hardware malfunction determination. The primary ethanol concentration and hardware malfunction determination includes detecting an air-fuel ratio during a pre-fuel mix period and learning the air-fuel ratio detected during the pre-fuel mix period as a current hardware reference value. The pre-fuel mix period is a period during which only flexible fuel which has not mixed with flexible fuel from the refuel event is being consumed by a vehicle engine. A hardware reference value difference is determined between the current hardware reference value and a previous hardware reference value from an immediately preceding vehicle driving cycle occurring prior to the refueling event. When the hardware reference value difference is greater than or equal to a predetermined hardware reference value threshold, a hardware malfunction is detected. When the hardware reference value difference is less than the predetermined hardware reference value threshold, the air-fuel ratio during a post-fuel mix period following the pre-fuel mix period is detected, and an ethanol concentration is learned based on the air-fuel ratio detected during the post-fuel mix period.

According to another aspect, a method for determining a flexible fuel ethanol concentration and detecting a hardware malfunction is provided. The method includes, immediately following start-up of a vehicle, detecting whether a refuel event has occurred and detecting a vehicle temperature. When the occurrence of the refuel event is detected and the vehicle temperature is detected to be less than a vehicle temperature threshold value, a cold-start ethanol concentration and hardware malfunction determination is performed. The cold-start ethanol concentration and hardware malfunction determination includes continuously detecting an air-fuel ratio during a fuel mixing period following a pre-fuel mix period and prior to a post-fuel mix period, and calculating an observed slope of the air-fuel ratio detected during the fuel mixing period over an amount of fuel consumed during the fuel mixing period. A slope difference between the observed slope and a predetermined expected slope is determined, and when the slope difference is greater than or equal to a predetermined slope difference threshold value, a hardware malfunction is detected. When the slope difference is less than the predetermined slope difference threshold value, the air-fuel ratio during the post-fuel mix period is detected, and an ethanol concentration is learned based on the air-fuel ratio detected during the post-fuel mix period.

According to still another aspect, a vehicle controller for detecting a flexible fuel ethanol concentration and hardware malfunction includes a refuel detecting section and a flexible fuel ethanol concentration and hardware malfunction detecting unit. The refuel detecting section is configured to receive a vehicle fuel level input from a vehicle fuel sensor and to determine whether a refuel event has occurred based upon the received vehicle fuel level input. The flexible fuel ethanol concentration and hardware malfunction detecting unit is configured to receive an air-fuel ratio input from a vehicle air-fuel sensor, and to perform primary ethanol concentration and malfunction determination when the refuel detecting section determines that the refuel event has occurred. The primary ethanol concentration and malfunction determination includes learning a current hardware reference value as the air-fuel ratio input during a pre-fuel mix period, the pre-fuel mix period being a period during which only flexible fuel which has not mixed with the flexible fuel from the refuel event is being consumed by a vehicle engine, and determining a hardware reference value difference as a difference between the current hardware reference value and a previous hardware reference value stored from the immediately preceding vehicle driving cycle occurring prior to the refueling event. When the hardware reference value difference is greater than or equal to a predetermined hardware reference value threshold, a hardware malfunction is detected. When the hardware reference value difference is less than the predetermined hardware reference value threshold, an ethanol concentration is learned based on the air-fuel ratio input during a post-fuel mix period following the pre-fuel mix period.

DETAILED DESCRIPTION

Figure 1:
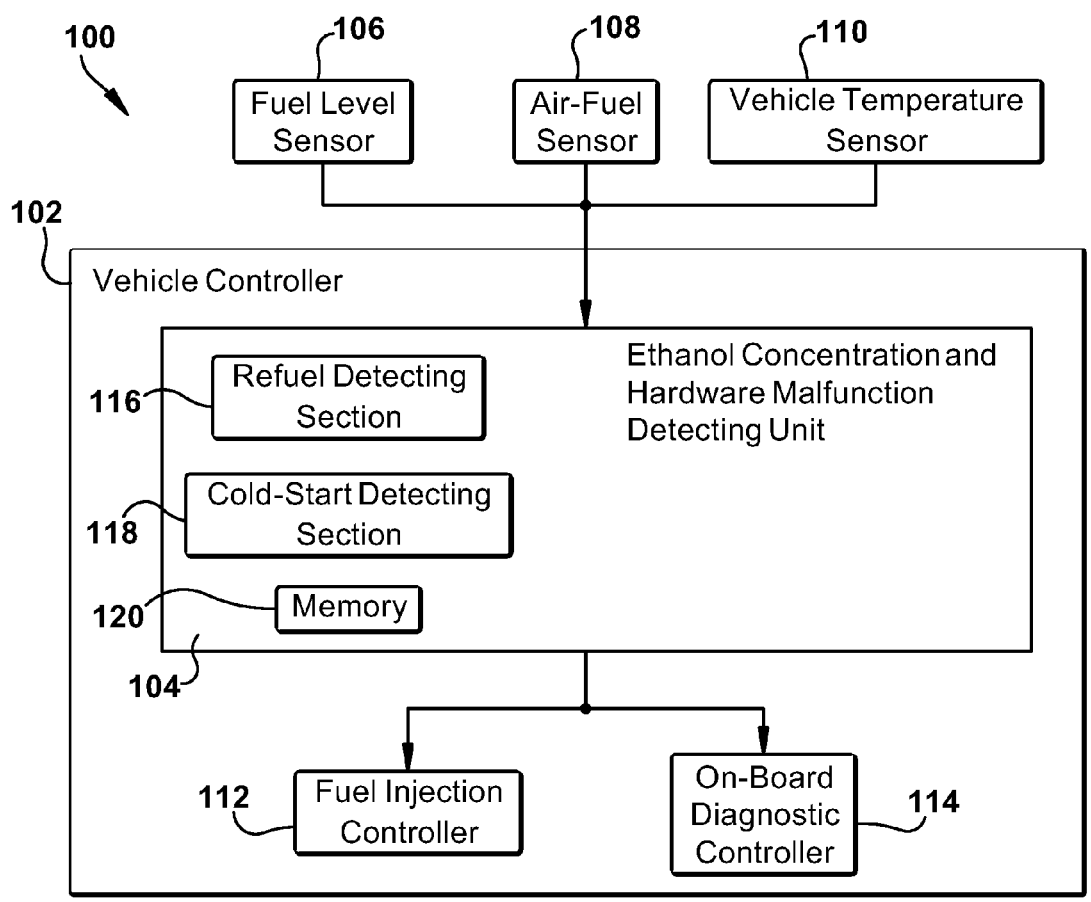
FIG. 1 is a block schematic illustrating an ethanol concentration and hardware malfunction detecting system.

FIG. 1 shows an ethanol concentration and hardware malfunction detecting system 100 (hereinafter, "system 100") which is implemented via a vehicle controller 102. The system 100 and vehicle controller 102 may be provided in a flexible fuel vehicle configured to operate using a flexible fuel which is a mixture of gasoline and ethanol. With respect to the flexible fuel, an ethanol concentration in the flexible fuel may vary following the addition of new flexible fuel during a refuel event, and the system 100 is configured to learn the ethanol concentration following the refuel event and/or upon occurrence of any other event which may trigger a change in ethanol concentration. More particularly, the system 100 is configured to learn or determine the ethanol concentration of the flexible fuel based on a detected air-fuel ratio feedback from consumed flexible fuel. The system 100 is also configured to detect a hardware malfunction, and to distinguish a detected change in flexible fuel ethanol concentration from the hardware malfunction.

The vehicle controller 102 may take the form of one or more processors (and/or other hardware elements) configured to monitor and control various vehicle functions. For example, the one or more processors of the vehicle controller 102 may have software stored therein which causes the vehicle controller 102 to execute control programs to monitor and control the various vehicle functions. The vehicle controller 102 of this type may be generally known in the art and therefore will only be described as is relevant to the system 100.

With regard to the system 100, as shown in FIG. 1 the vehicle controller 102 includes an ethanol concentration and hardware malfunction detecting unit 104 (hereinafter, "detecting unit 104") and is in communication with at least a fuel level sensor 106, an air-fuel sensor 108, and a vehicle temperature sensor 110. The vehicle controller 102 also includes a fuel injection controller 112 and an on-board diagnostic controller 114 which are in communication with the detecting unit 104.

The detecting unit 104 may be implemented via one or more processors (and/or other hardware elements) which may run software implemented control programs so as to determine ethanol concentration and detect a hardware malfunction. It is to be appreciated that the detecting unit 104 may be provided as a hardware unit and/or via software within the vehicle controller 102, or as a hardware unit separate from the vehicle controller 102. The control program and processing performed by the detecting unit 104 is described in further detail below.

The fuel level sensor 106 may take the form of any sensor capable of monitoring and/or measuring a fuel level in a vehicle fuel tank (not shown). Fuel sensors of this type are considered to be generally known in the art, and as such the particular details of the fuel level sensor 106 will not be described herein. With respect to the system 100, the fuel level sensor 106 may monitor the fuel level in the vehicle fuel tank, may operate in conjunction with the vehicle controller 102 to determine an amount of fuel consumed by a vehicle engine (not shown), and/or may independently determine the amount of fuel consumed by the vehicle engine. For example, with respect to determining the amount of fuel consumed, the fuel level sensor 106 may continuously communicate a fuel level input to the vehicle controller 102, and the vehicle controller 102 may use the continuously communicated fuel level input to determine the amount of fuel consumed based on a change in the fuel level.

The air-fuel sensor 108 may take the form of any sensor capable of sensing an air-fuel ratio. The air-fuel sensor 108 may be provided in a vehicle exhaust system so as to detect the air-fuel ratio for vehicle exhaust gas. Air-fuel sensors of this type are considered to be generally known in the art, and as such the particular details of the air-fuel sensor 108 will not be described herein. With respect to the system 100, the air-fuel sensor 108 senses or detects the air-fuel ratio for vehicle exhaust gas and communicates an air-fuel ratio input signal to the vehicle controller 102 and the detecting unit 104.

The vehicle temperature sensor 110 may take the form of any sensor capable of sensing a vehicle temperature. The vehicle temperature sensor 110 may be provided to sense a vehicle engine temperature. Vehicle temperature sensors of this type are considered to be generally known in the art, and as such the particular details of the vehicle temperature sensor 110 will not be described herein. With respect to the system 100, the vehicle temperature sensor 110 senses or detects the vehicle temperature and communicates a vehicle temperature input signal to the vehicle controller 102 and the detecting unit 104.

The fuel injection controller 112 may take the form of any controller capable of controlling a fuel injection of the vehicle. Fuel injection control and controllers of this type are considered to be generally known in the art, and as such the particular details of the fuel injection control and the fuel injection controller 112 will not be described in detail herein. As shown in FIG. 1, the fuel injection controller 112 communicates with (i.e., receives an input from) the vehicle controller 102 and the detecting unit 104. Particularly, the vehicle controller 102 and the detecting unit 104 transmit a signal to the fuel injection controller 112 indicating the ethanol concentration of the flexible fuel determined by the detecting unit 104. The input ethanol concentration of the flexible fuel is used by the fuel injection controller 112 to determine and control the fuel injection.

It is to be appreciated that the fuel injection controller 112 may also receive other inputs related to fuel injection control from the vehicle controller 102 and/or other sources. Furthermore, fuel injection control instructions may be determined by the vehicle controller 102, a subcomponent of the vehicle controller 102, or a separate element which communicates with the vehicle controller 102, and transmitted to the fuel injection controller 112, which controls fuel injection based on the instruction received from the vehicle controller 102. It is also to be appreciated that the fuel injection controller 112 may be incorporated in the vehicle controller 102, as shown in FIG. 1, or provided separately from the vehicle controller 102.

The on-board diagnostic controller 114 may take the form of any controller capable of monitoring or detecting various vehicle malfunctions or condition states which may necessitate or warrant notification. Such notification events may be determined or detected by the vehicle controller 102 and/or the on-board diagnostic controller 114 based on inputs received from various vehicle sensors, including the fuel level sensor 106, the air-fuel sensor 108, and/or the vehicle temperature sensor 110. In this regard, the on-board diagnostic controller 114 may be configured to determine or detect the notification event, and/or to receive a notification event input from the vehicle controller 102 which determines or detects the notification event. When the notification event is determined or detected (and the notification event input is received by the on-board diagnostic controller 114 when determination is made by the vehicle controller 102), the on-board diagnostic controller 114 may instruct a malfunction indicator lamp (not shown) to light up in a vehicle passenger compartment so as to notify a user of the vehicle in one embodiment, though notification may be alternately provided within the vehicle (e.g., through an on-screen display, through one or more other visual indicators, through voice or sound notification, etc.). On-board diagnostic control and controllers of this type are considered to be generally known in the art, and as such the particular details of the on-board diagnostic controller 114 will not be described in detail herein.

With respect to the system 100, one such notification event may include the hardware malfunction detected by the detecting unit 104, i.e., the hardware malfunction of any vehicle component related to the determination of the flexible fuel ethanol concentration and/or fuel injection control. In this regard, as shown in FIG. 1 the on-board diagnostic controller 114 is in communication with the vehicle controller 102 and detecting unit 104. The vehicle controller 102 and detecting unit 104 transmit a signal to the on-board diagnostic controller 114 when the hardware malfunction is detected such that the on-board diagnostic controller 114 may notify the user of the vehicle (e.g., by lighting the malfunction indicator lamp).

As used herein, the hardware malfunction may refer to the failure or improper operation of any vehicle component related to the determination of the flexible fuel ethanol concentration and/or fuel injection control. For example, the hardware malfunction referenced herein may refer to a malfunction of any one or more of the vehicle controller 102, the fuel level sensor 106, the air-fuel sensor 108, the vehicle temperature sensor 110, the fuel injection controller 112, the on-board diagnostic controller 114, and/or any other vehicle component.

It is to be appreciated that the fuel level sensor 106, the air-fuel sensor 108, the vehicle temperature sensor 110, the fuel injection controller 112, and onboard diagnostic controller 114 may be incorporated in the vehicle controller 102 and/or may be provided separately from the vehicle controller 102. It is also to be appreciated that the functions performed by the fuel level sensor 106, the air-fuel sensor 108, the vehicle temperature sensor 110, the fuel injection controller 112, and the on-board diagnostic controller 114 may be performed by different mechanisms, such as those used to estimate and/or determine certain features based on directly or indirectly related factors. The instant disclosure will focus on the function performed by and the operation of these components as they relate to the operation of the system 100, with particular reference to their interaction with the detecting unit 104.

Returning to the detecting unit 104, it is noted that a refuel detecting section 116, a cold-start detecting section 118, and a memory 120 may be provided therein or thereby. The refuel detecting section 116, the cold-start detecting section 118, and the memory 120 may be provided as hardware elements within or separate from the detecting unit 104, or may be incorporated in the detecting unit 104 via software control programs which cause the detecting unit 104 to perform the functions thereof.

As noted above, the detecting unit 104 is configured to perform processing to determine the ethanol concentration of the flexible fuel in the vehicle fuel tank, and to detect the hardware malfunction. As will be evident with reference to the below description, the processing performed by the detecting unit 104 may utilize a detection of a refuel event of the vehicle by the refuel detecting section 116. Detection of the refuel event may be based on the fuel level input received from the fuel level sensor 106. The detection of the refuel event is made, and may be relevant to the below-described processing, because the introduction of new flexible fuel may be the most likely impetus for a change in the ethanol concentration of the flexible fuel in the vehicle fuel tank.

Similarly, the processing performed by the detecting unit 104 may utilize a detection of whether the vehicle is being started in a cold-start condition by the cold-start detecting section 118. Detection of the cold-start condition may be based on the vehicle temperature input received from the vehicle temperature sensor 110. As is described in further detail below, the detection of the flexible fuel ethanol concentration may be affected during cold operation of the vehicle engine.

The memory 120 may take the form of any writable computer memory, and is configured to store various vehicle fuel level inputs, vehicle temperature inputs, and air-fuel ratio inputs at particular various times of vehicle operation. To facilitate such storage into the memory 120, as well as the performance of the below-described processing, the detecting unit 104 and/or vehicle controller 102 may be configured to detect a vehicle start-up and/or a vehicle power-off. Such functionality is considered to be known in the art, and will therefore not be described in detail herein.

With particular respect to the determination of the ethanol concentration in the flexible fuel and the detection of the hardware malfunction, the detecting unit 104 is configured to perform any one or more of a primary ethanol concentration and hardware malfunction determination, a secondary ethanol concentration and hardware malfunction determination, and a cold-start ethanol concentration and hardware malfunction determination depending on various conditions detected immediately following a start-up of the vehicle and/or detection of a refuel event while the vehicle is running. Particularly, the detecting unit 104 may perform one of the primary, secondary, and cold-start ethanol concentration and hardware malfunction determinations based on whether a refuel event and/or a cold-start condition is detected.

Figure 2:
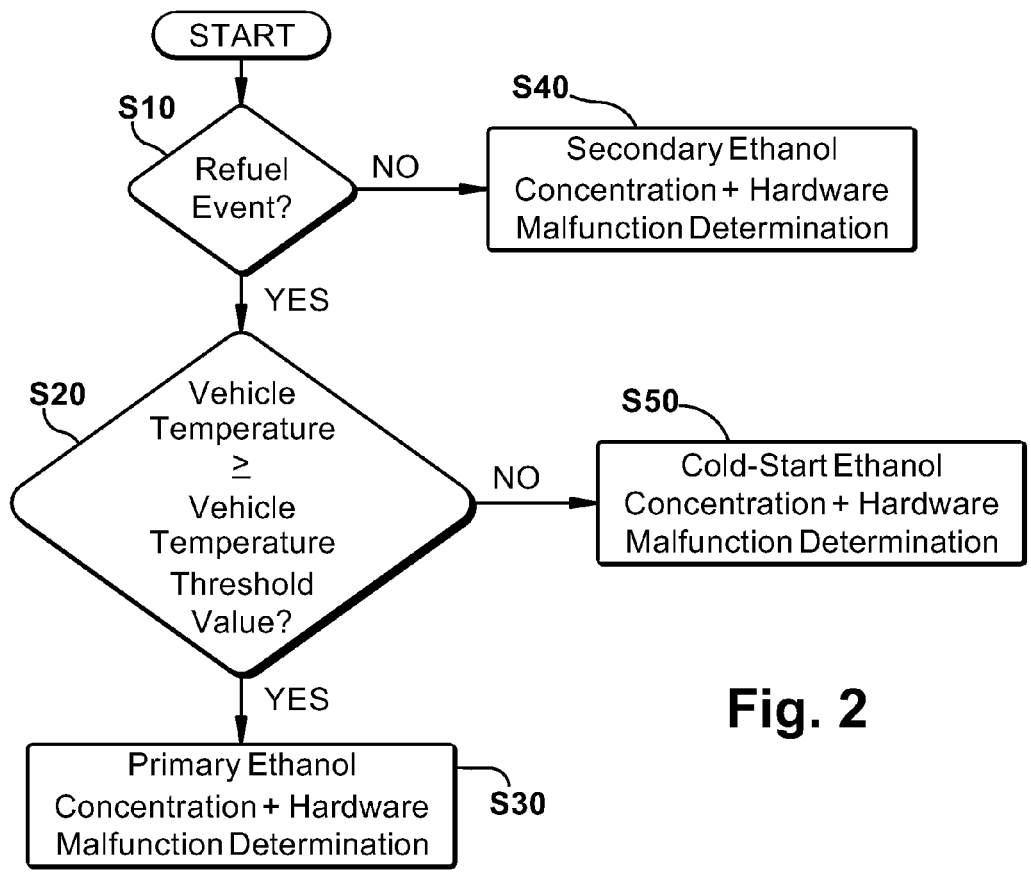
FIG. 2 is a flowchart illustrating a method of operation for the ethanol concentration and hardware malfunction detecting system.

With reference to FIG. 2, a method for determining which of the primary, secondary, and cold-start ethanol concentration and hardware malfunction determinations is to be performed is shown. The method begins with the detecting unit 104 detecting whether a refuel event has occurred (S10) via the refuel detecting section 116. The detection of whether the refuel event has occurred may be performed immediately following start-up of the vehicle.

To detect whether the refuel event has occurred, the detecting unit 104, via the refuel detecting section 116, compares a previous fuel level with a current fuel level. The previous fuel level is a fuel level measured and/or sensed by the fuel level sensor 106 at a conclusion of an immediately preceding vehicle driving cycle, and stored in the memory 120. As used herein, the immediately preceding vehicle driving cycle may correspond to a vehicle driving cycle, which includes a start-up and power-off of the vehicle, immediately preceding a current start-up of the vehicle. The fuel level sensor 106 measures or senses the fuel level at a time of or immediately preceding the power-off the vehicle during the immediately preceding vehicle driving cycle, and the detecting unit 104 receives and stores this vehicle fuel level input in the memory 120 as the previous fuel level. Afterwards, immediately following the next start-up of the vehicle (i.e., the start-up of the vehicle immediately after the power-off of the vehicle during which the previous fuel level was measured and stored), the fuel level sensor 106 measures or senses the fuel level in the vehicle fuel tank, and uses the measured or sensed fuel level as the current fuel level.

In the described embodiment, the refuel detecting section 116 can then compare the previous fuel level and the current fuel level to determine whether the refuel event has occurred. When a difference between the previous fuel level and the current fuel is greater than or equal to a predetermined fuel level difference, the occurrence of the refuel event is detected by the refuel detecting section 116. When the difference between the previous fuel level and the current fuel level is less than the predetermined fuel level difference, the occurrence of the refuel event is not detected by the refuel detecting section 116, or is detected as not having occurred.

While the detection of the refueling event is described above as taking place upon start-up of the vehicle, the herein-described system and method may also detect the refueling event when refueling occurs while the vehicle is running (i.e., the vehicle is not turned off for refueling). To detect the refueling event that takes place without turning off the vehicle, the fuel level may be continuously monitored by the fuel level sensor 106, and the inputs from the fuel level sensor 106 may directed to the refuel detecting section 116. The refuel detecting section 116 may then determine whether a refueling event has occurred based on an increase in the fuel level based on inputs from the fuel level sensor 106. The refuel detecting section 116 may also consider additional variables, such as whether the increase in fuel level measured by the fuel level sensor 106 is concurrent with the vehicle being stopped for at least a predetermined time period that would indicate the vehicle is being refueled. In such a configuration, the immediately preceding driving cycle may correspond to a vehicle driving cycle occurring prior to refueling of the vehicle (e.g., immediately prior to the detection of the refueling of the vehicle while the vehicle is running). As will be appreciated by those skilled in the art, a refuel event may be detected otherwise than as described herein, and detecting whether the refuel event has occurred in S10 is intended to encompass all manners of detecting a refuel event. It is also to be appreciated that detection of the refueling event may take place both immediately following start-up of the vehicle and while the vehicle is running. Accordingly, the immediately preceding driving cycle may correspond to both the vehicle driving cycle occurring prior to refueling of the vehicle and the vehicle driving cycle, which includes the start-up and power-off of the vehicle, immediately preceding the current start-up of the vehicle.

When the occurrence of the refuel event is detected (S10: Yes) immediately following start-up of the vehicle, the detecting unit 104 continues to determine whether the vehicle is being started in the cold-start condition (S20). To detect whether the vehicle is being started in the cold-start condition, the vehicle temperature sensor 110 measures or senses the vehicle temperature (e.g., the vehicle engine temperature) immediately following start-up of the vehicle. The detecting unit 104 and cold-start detecting section 118 receive this vehicle temperature input, and compare the vehicle temperature immediately following start-up of the vehicle with a vehicle temperature threshold value. When the vehicle temperature immediately following start-up of the vehicle is greater than or equal to the vehicle temperature threshold value, the cold-start detecting section 118 detects that the vehicle is not being started in the cold-start condition (S20: YES). However, when the vehicle temperature immediately following start-up of the vehicle is less than the vehicle temperature threshold valve, the cold-start detecting section 118 detects that the vehicle is being started in the cold-start condition (S20: NO).

When the detecting unit 104, via the refuel detecting section 116 and the cold-start detecting section 118, detects that the refuel event has occurred (S10: Yes) and that the vehicle is not being started in the cold-start condition (S20: YES), the detecting unit 104 performs the primary ethanol concentration and hardware malfunction determination (S30). When the detecting unit 104 detects that the refuel event has not occurred (S10: No), the detecting unit 104 performs the secondary ethanol concentration and hardware malfunction determination (S40). When, immediately following start-up of the vehicle, the detecting unit 104 detects that the refuel event has occurred (S10: Yes) and that the vehicle has been started in the cold-start condition (S20: No), the detecting unit 104 performs the cold-start ethanol concentration and hardware malfunction determination.

Figure 3:
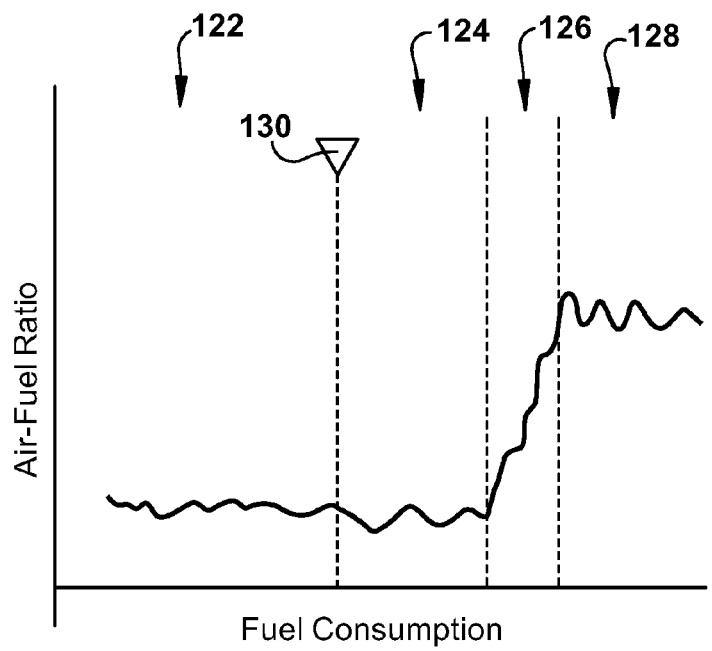
FIG. 3 is a graph showing air-fuel ratio over fuel consumption over a pre-fuel mix period, a fuel mixing period, and a post-fuel mix period.

The primary ethanol concentration and hardware malfunction determination will be described with reference to FIGS. 3 and 4. FIG. 3 is a graph illustrating an example of the air-fuel ratio detected by the air-fuel sensor 108 over a fuel consumption of the flexible fuel by the vehicle engine. With particular reference to the graph of FIG. 3, it is noted that there are four periods relevant to the ethanol concentration and hardware malfunction detection in the illustrated example. Specifically, there is an immediately preceding vehicle driving cycle period 122 (hereinafter, "first period 122" or "immediately preceding vehicle driving cycle"), a pre-fuel mix period 124, a fuel mixing period 126, and a post-fuel mix period 128. It is to be appreciated that the refueling of the vehicle, in the illustrated example, occurs between the immediately preceding driving cycle period 122 and the pre-fuel mix period 124. In this regard, a vehicle refuel event 130 is noted on the graph of FIG. 3, and serves as a demarcation between the immediately preceding vehicle driving cycle period 122 and the pre-fuel mix period 124.

In this regard, the refuel event 130 may correspond to a power-off to start-up time of the vehicle during refueling (i.e., when the vehicle is powered-off for refueling), or it may correspond to the period of refueling while the vehicle is running. In either case, the immediately preceding vehicle driving cycle period 122 refers to the period before the refuel event 130, and the pre-fuel mix period 124 refers to the period following (and/or concurrent with) the refuel event 130.

Following the introduction of new flexible fuel to the vehicle fuel tank during the refuel event 130, the newly introduced fuel from the refuel event 130 mixes with existing fuel in the vehicle fuel tank. Insofar as fuel introduced during the refuel event 130 may have a different ethanol concentration than the fuel in the vehicle fuel tank, the ethanol concentration of the flexible fuel consumed by the vehicle engine may change. In this regard, the change in the ethanol concentration of the flexible fuel being consumed by the vehicle engine changes in varying amounts through the pre-fuel mix period 124, the fuel mixing period 126, and the post-fuel mix period 128.

The pre-fuel mix period 124 is a period during which none of the fuel from the refuel event 130 is being consumed by the vehicle engine. Alternatively stated, in the case where the vehicle is powered-off for refueling, the pre-fuel mix period 124 is a period during which only flexible fuel in a vehicle fuel line immediately prior to start-up of the vehicle (or power-off of the vehicle during the immediately preceding vehicle driving cycle) is being consumed by the vehicle engine. It is to be appreciated that upon power-off of the vehicle from the immediately preceding vehicle driving cycle, a certain amount of flexible fuel is disposed in the vehicle fuel lines. The flexible fuel in the vehicle fuel lines will not mix with the flexible fuel introduced during the refuel event. The pre-fuel mix period 124 corresponds to the period during which only flexible fuel in the vehicle fuel lines at the time of power-off of the immediately preceding vehicle driving cycle (i.e., at the time of start-up of a current vehicle driving cycle) is consumed. There will generally be a known volume of fuel in the fuel lines and so it can be precisely determined or estimated as to when the pre-fuel mix period 124 ends. For example, the vehicle fuel lines may contain approximately 0.1 liters of flexible fuel and therefore the pre-fuel mix period 124 may cover a fuel consumption of 0.1 liters.

When the refuel event 130 is carried out while the vehicle is running, the pre-fuel mix period 124 may correspond to a period that is any one or more of a time during the refuel event 130 and a time immediately following the refuel event 130. Similar to the case where the vehicle is powered-off for refueling, the pre-fuel mix period 124 corresponds to the period during which only flexible fuel in the vehicle fuel lines which has not mixed with flexible fuel from the refuel event 130 (i.e., which does not include any fuel from the refuel event 130) is consumed. The pre-fuel mix period 124 may have a different duration in the case of refueling while the vehicle is running than in the case of refueling while the vehicle is powered-off. However, in either case, there will generally be a known volume of fuel in the fuel lines and so it can be precisely determined or estimated as to when the pre-fuel mix period 124 ends.

Thereafter, flexible fuel from the refuel event 130 mixes with existing flexible fuel in the vehicle fuel tank from before the refuel event 130 while the mixing fuel is transmitted to and consumed by the vehicle engine. During this period, i.e., the fuel mixing period 126, the flexible fuel from the refuel event 130 is in the process of mixing with the flexible fuel in the vehicle fuel tank from before the refuel event 130, and the flexible fuel being consumed by the vehicle engine may have a variable proportion of flexible fuel introduced during the refuel event 130 to flexible fuel previously in the vehicle fuel tank. As such, the concentration of ethanol in the flexible fuel being consumed by the vehicle engine may therefore also be variable. Following the fuel mixing period 126, the flexible fuel introduced from the refuel event 130 has fully mixed with (or can be considered as having fully mixed with) the flexible fuel previously existing in the vehicle fuel tank, and fully mixed flexible fuel in the vehicle fuel tank settles to a consistent ethanol concentration which is consumed by the vehicle engine. This last period is the post-fuel mixing period 128.

With general respect to the determination of the ethanol concentration in the flexible fuel, it is reiterated that the determination is made based on a relationship between the air-fuel ratio detected by the air-fuel sensor 108 and the ethanol concentration of the flexible fuel consumed by the vehicle engine. The relationship between the air-fuel ratio and the ethanol concentration of the flexible fuel may be experimentally or theoretically determined, and/or may be determined based on known relationships between the two. Accordingly, as the ethanol concentration of the flexible fuel changes, the air-fuel ratio detected by the air-fuel sensor 108 will correspondingly change. Therefore, as shown in the graph of FIG. 3, the air-fuel ratio detected by the air-fuel sensor 108 changes between the pre-fuel mix period 124, the fuel mixing period 126, and the post-fuel mix period 128. The herein described ethanol concentration and hardware malfunction determination is performed based on expected and observed changes in the air-fuel ratio sensed by the air-fuel sensor 108 over the fuel consumption and across the pre-fuel mix period 124, the fuel mixing period 126, and the post-fuel mix period 128.

Figure 4:
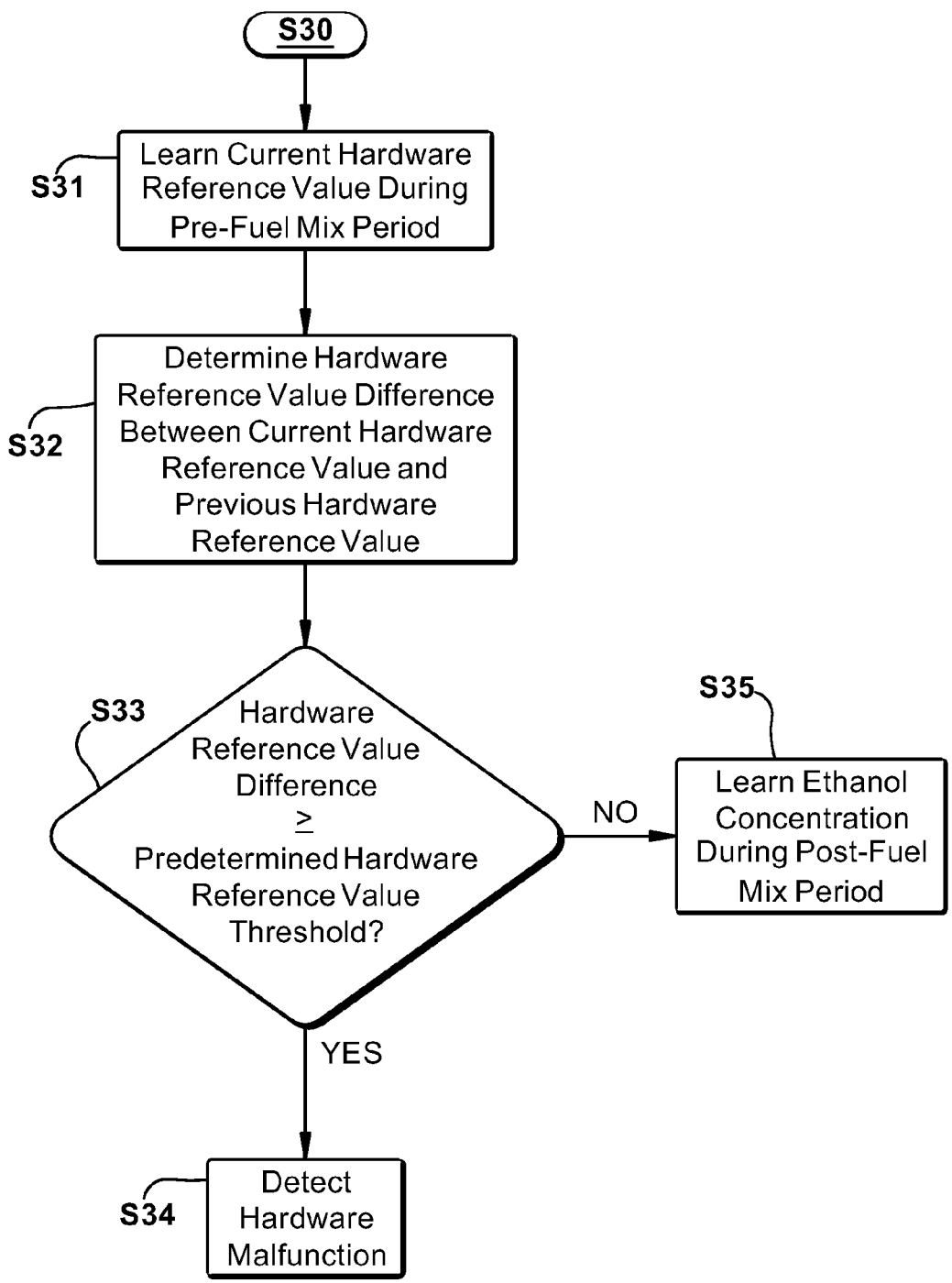
FIG. 4 is a flowchart illustrating a primary ethanol concentration and hardware determination method.

Turning to FIG. 4, the primary ethanol concentration and hardware malfunction determination includes detecting the air-fuel ratio using the air-fuel sensor 108 immediately following start-up of the vehicle or upon detection of the refuel event 130 when the refuel event 130 takes place while the vehicle is running. As will be appreciated with reference to FIG. 3, this period corresponds to the pre-fuel mix period 124. This detected air-fuel ratio input is received by the detecting unit 104 and learned as a current hardware reference value (S31). Furthermore, the air-fuel ratio is detected by the air-fuel sensor 108 during the immediately preceding driving cycle (i.e., during the first period 122), and the associated air-fuel ratio input is received by the detecting unit 104 and stored in the memory 120 as a previous hardware reference value (S31). It is noted that the previous hardware reference value may be learned and stored in the memory 120 at or immediately before each power-off of the vehicle (for use immediately following start-up of the vehicle) and/or periodically during the immediately preceding driving cycle period 122 (for use when the refuel event 130 takes place while the vehicle is running).

As the flexible fuel consumed by the vehicle engine during the pre-fuel mix period 124 is in the vehicle fuel lines at the conclusion of the immediately preceding vehicle driving cycle (i.e., the first period 122) and/or before/during/immediately after the refueling event 130, and does not mix with the flexible fuel introduced from the refuel event 130, the current hardware reference value should substantially equal the previous hardware reference value. This is because the air-fuel ratio detected by the air-fuel sensor 108 at the conclusion of the immediately preceding vehicle driving cycle and immediately following start-up and/or refueling of the vehicle is based on the consumption of flexible fuel having an identical ethanol concentration.

Accordingly, following the learning of the current hardware reference value (S31), the detecting unit 104 determines a hardware reference value difference as the difference between the current hardware reference value and the previous hardware reference value (S32). The detecting unit 104 then compares the hardware reference value difference with a predetermined hardware reference value threshold (S33). The predetermined hardware reference value threshold is determined as a difference value between the current and previous hardware reference values which is sufficiently significant to indicate that a hardware malfunction may exist (e.g., in the ethanol concentration detecting unit 104, air-fuel sensor 108, fuel injection controller 112, and/or any other vehicle components related to ethanol concentration determination and fuel injection control/operation).

When the hardware reference value difference is greater than the predetermined hardware reference value threshold (S33: Yes), the detecting unit 104 detects the hardware malfunction (S34). However, when the hardware reference value difference is less the predetermined hardware reference value threshold (S33: No), then the detecting unit 104 does not detect the hardware malfunction and continues to learn the ethanol concentration of the flexible fuel (S35). To learn the ethanol concentration of the flexible fuel, the air-fuel sensor 108 detects the air-fuel ratio during the post-fuel mix period 128, and determines (i.e., calculates) the ethanol concentration based on the air-fuel ratio detected during the post-fuel mix period 128 (S35).

Figure 5:
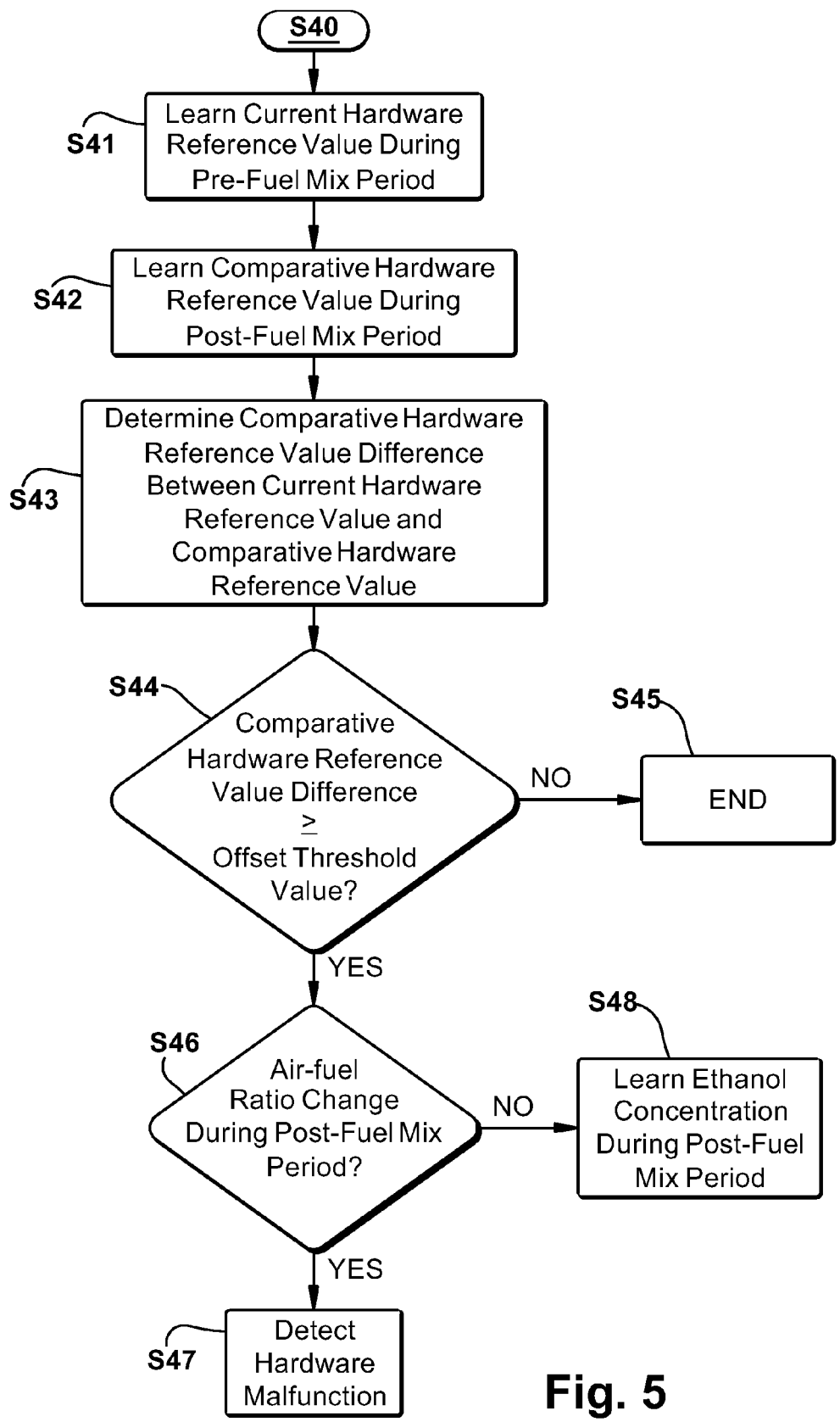
FIG. 5 is a flowchart illustrating a secondary ethanol concentration and hardware determination method.

In certain situations, it is possible that the detecting unit 104 (via the refuel detecting section 116) may not detect the refuel event 130 even though the refuel event 130 has occurred. Particularly, the detecting unit 104 and the refuel detecting section 116 may not detect the refuel event 130 though the refuel event 130 has occurred if there is a malfunction with the fuel level sensor 106 and/or if a refuel amount is relatively small and therefore does not exceed or is very close to the predetermined fuel level difference. In such a situation, the ethanol concentration and hardware malfunction detection processing may not be triggered to perform the primary ethanol concentration and hardware malfunction determination (FIG. 4). Even when this is the case, the detecting unit 104 is configured to perform the secondary ethanol concentration and hardware malfunction determination shown in FIG. 5.

In the secondary ethanol concentration and hardware malfunction detecting processing, which may be performed immediately following start-up of the vehicle (or periodically, continuously, or upon a trigger while the vehicle is running), the air-fuel ratio during the pre-fuel mix period 124 is detected by the fuel level sensor 106, and the associated air-fuel ratio input is received by the detecting unit 104 and learned as the current hardware reference value (S41). Furthermore, the air-fuel ratio is also detected by the air-fuel sensor 108 during the post-fuel mix period 128, and the associated air-fuel ratio input is received by the detecting unit 104 and learned as a comparative hardware reference value (S42). The detecting unit 104 then determines a comparative hardware reference value difference as the difference between the current hardware reference value and the comparative hardware reference value (S43).

The detecting unit 104 compares the hardware reference value difference with a predetermined offset threshold value (S44). The predetermined offset threshold value is a value indicative of a change in air-fuel ratio which would correspond to a refuel event, and may be determined experimentally and/or theoretically via known relationships between air-fuel ratio and flexible fuel ethanol concentration. Generally, the predetermined offset threshold value is set as a value outside of a normal or expected range of fluctuation in the air-fuel ratio detected by the air-fuel sensor 108 when flexible fuel with a substantially consistent concentration is being consumed by the vehicle engine. Accordingly, when the comparative hardware reference value difference is less than the predetermined offset threshold value (S44: No), the secondary ethanol concentration and hardware malfunction determination processing determines that the refuel event has not occurred, and that the ethanol concentration of the flexible fuel in the vehicle fuel tank has not changed. Therefore, the secondary ethanol concentration and hardware malfunction determination processing ends (S45).

However, when the comparative hardware reference value difference is greater than the predetermined offset threshold value (S44: Yes), the detecting unit 104 continuously monitors the air-fuel ratio detected by the air-fuel sensor 108 during the post-fuel mix period. If the air-fuel ratio during the post-fuel mix period is detected to change by greater than a predetermined air-fuel malfunction threshold (S46: yes), the detecting unit 104 detects a hardware malfunction (S47). However, when the air-fuel ratio detected during the post-fuel mix period does not change by more than the predetermined air-fuel malfunction threshold (S46: No), the detecting unit 104 learns the ethanol concentration of the flexible fuel based on the air-fuel ratio detected during the post-fuel mix period (S48). The predetermined air-fuel malfunction threshold is a threshold value determined experimentally or theoretically based on known relationships between air-fuel ratio and flexible fuel ethanol concentration, and may be set to a value greater than a normal or expected fluctuation in the detected air-fuel ratio assuming a consistent ethanol concentration in the flexible fuel (as is present during the post-fuel mix period 128).

In addition to situation where the detecting unit 104 (via the refuel detecting section 116) may not detect the refuel event 130 even though the refuel event 130 has occurred, other environmental factors may affect the processing for flexible fuel ethanol concentration and hardware malfunction determination. One such example occurs when vehicle start-up is made while the vehicle engine is cold, herein referenced as the cold-start condition. In the cold-start condition, the detecting unit 104 may not be able to reliably separate hardware malfunction from changes in ethanol concentration. This is because the air-fuel ratio detected during the cold-start condition may not be representative of that observed during detection for a fully warm engine due to several factors related to cold fuel evaporation and combustion characteristics. The detecting unit 104 is therefore configured to perform cold-start ethanol concentration and hardware malfunction determination, which is illustrated in the flowchart of FIG. 6.

With reference to the cold-start ethanol concentration and hardware malfunction determination, it is generally noted that during the fuel mixing period 126, the mixing of the flexible fuel has been observed to follow an expected trend. In other words, the mixing of the flexible fuel introduced during the refuel event 130 and the flexible fuel existing in the vehicle fuel tank prior to the refuel event 130 will take place in a manner which is capable of being predetermined or otherwise estimated. As the flexible fuel mixes, the air-fuel ratio detected by the air-fuel sensor 108 will reflect the change in ethanol concentration. By comparing the change in the ethanol concentration over the course of this period with an expected change, it can be determined whether the relevant hardware is properly detecting the flexible fuel mixing, and therefore that the hardware is functioning properly (i.e., not malfunctioning), or is not properly detecting the flexible fuel mixing, and therefore that the hardware is malfunctioning.

Figure 6:
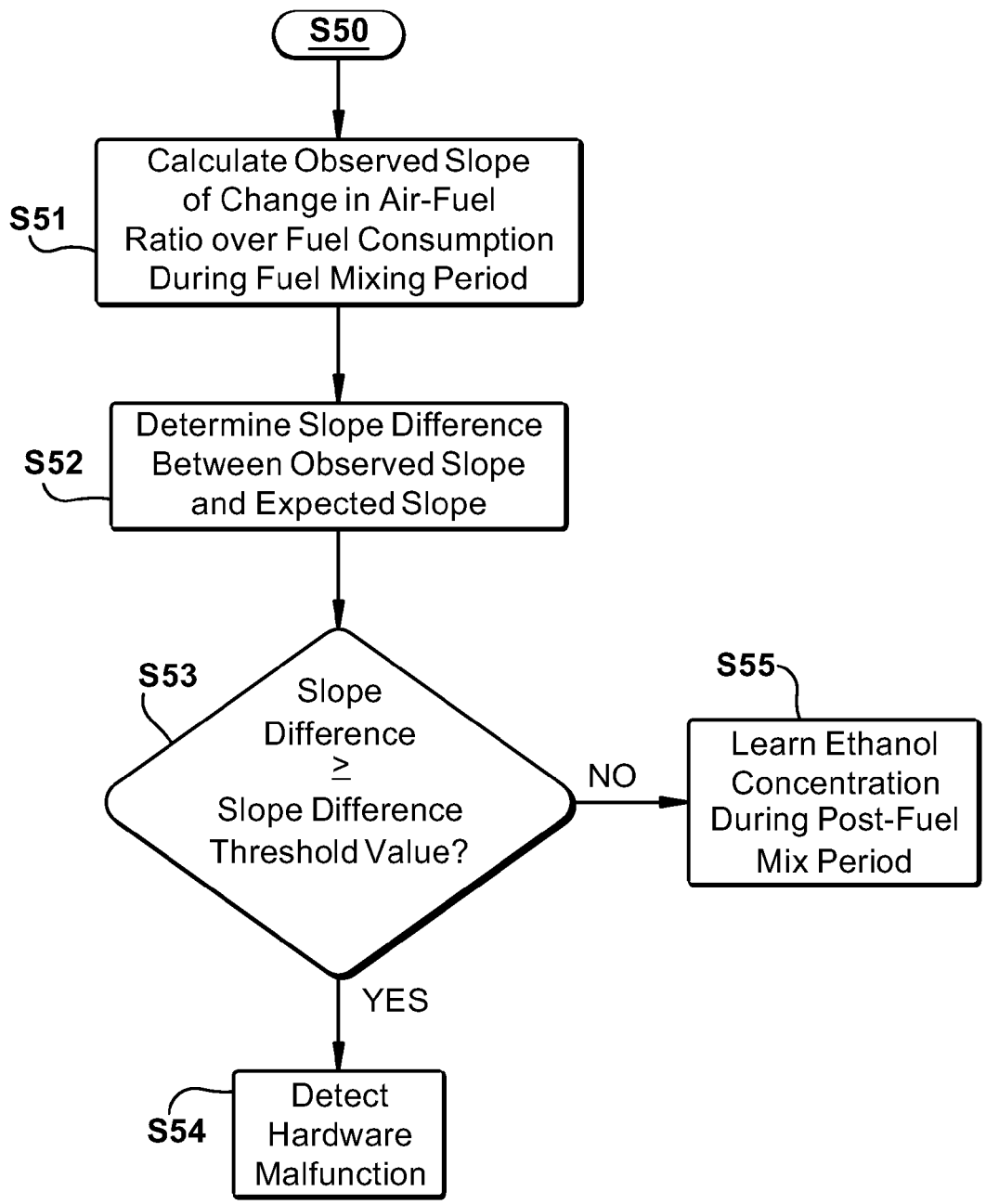
FIG. 6 is a flowchart illustrating a cold-start ethanol concentration and hardware determination method.

With reference to FIG. 6, it is noted that the cold-start ethanol concentration and hardware malfunction determination is triggered when the detecting unit 104 detects that the vehicle temperature immediately following start-up is less than the vehicle temperature threshold value (FIG. 2; S20). Once triggered, the detecting unit 104 and air-fuel sensor 108 continuously monitor and detect the air-fuel ratio during the fuel mixing period 126. Based on the detected air-fuel ratio during the fuel mixing period 126, a change of the air-fuel ratio over fuel consumption is calculated as an observed slope (S51). The observed slope of the air-fuel ratio over fuel consumption during the fuel mixing period 126 may be calculated using various methods. For example, a raw slope of the air-fuel ratio over consumed fuel may be used. Alternatively, the slope may be integrated (and later compared to a criteria value) or the slope of a least square best fit line over the fuel consumption may be used.

The detecting unit 104 then determines a slope difference as the difference between the observed slope and a predetermined expected slope for air-fuel ratio change during the fuel mixing period 126 (S52). As noted above, the expected slope may be set based on known flexible fuel mixing properties, or may be experimentally or theoretically determined as an expected flexible fuel mixing trend expressed as a detected change in the air-fuel ratio. By comparing the difference between the observed slope and the expected slope, a variance from an expected fuel mixing trend may be quantified. If the variance exceeds a normal, expected, and/or standard variance, then it may be determined that there is a hardware malfunction. However, if the variance does not exceed the normal, expected, and/or standard variance, then it may be concluded that the hardware is operating properly and the detecting unit 104 may continue to learn the ethanol concentration of the flexible fuel following the refuel event 130 during the post-fuel mix period 128.

Figure 7A:
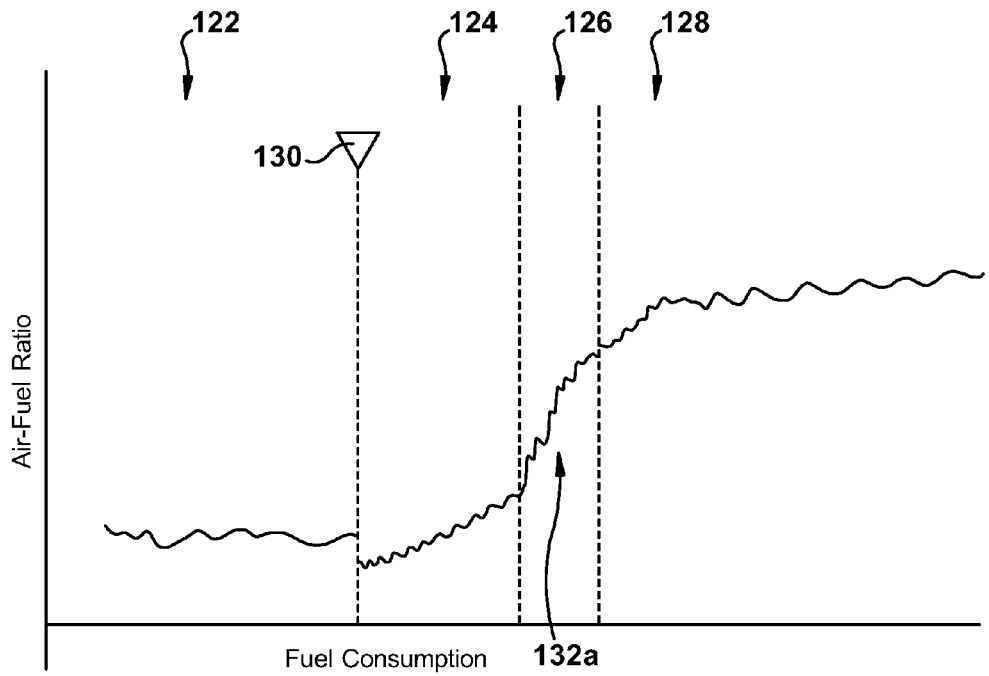
FIG. 7(a) is a graph showing air-fuel ratio over fuel consumption for a cold-start condition flexible fuel vehicle in which there is no hardware malfunction.
Figure 7B:
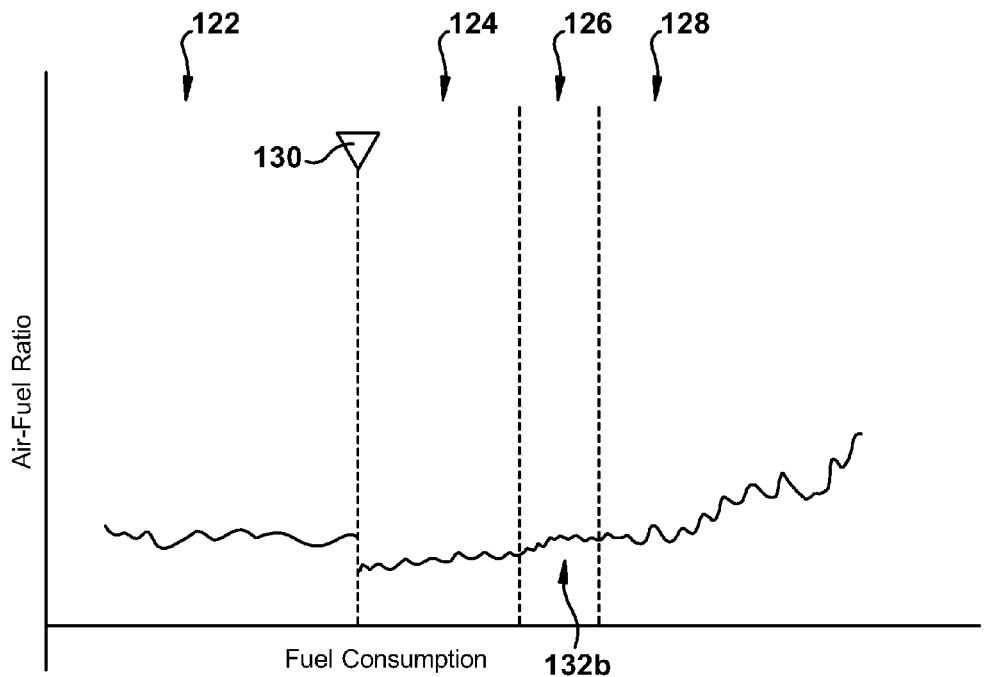
FIG. 7(b) is a graph showing air-fuel ratio over fuel consumption for a cold-start condition flexible fuel vehicle in which there is a hardware malfunction.
Figure 7C:
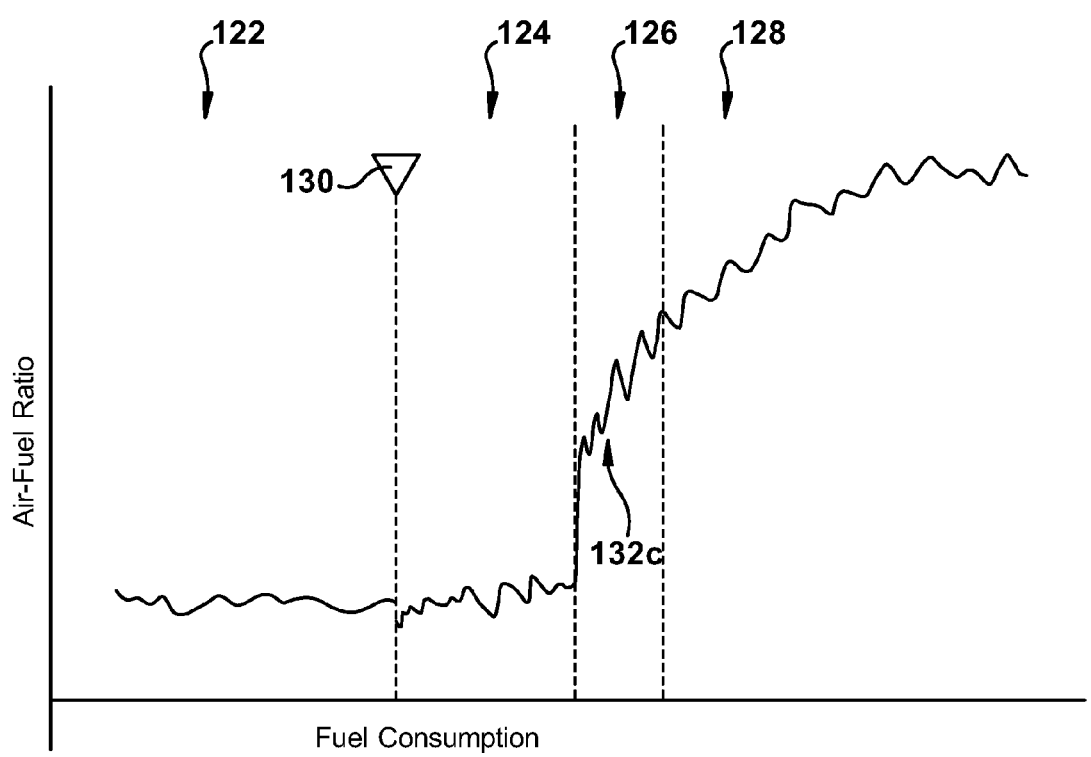
FIG. 7(c) is another graph showing air-fuel ratio over fuel consumption for a cold-start condition flexible fuel vehicle in which there is a hardware malfunction.

To illustrate detected air-fuel ratio changes during the fuel mixing period 126, reference is made to FIGS. 7(a) to 7(c). FIG. 7(a) graphically illustrates an exemplary detected air-fuel ratio over fuel consumption for a cold-start condition flexible fuel vehicle in which there is no hardware malfunction, and FIGS. 7(b) and 7(c) graphically illustrate exemplary detected air-fuel ratios for the cold-start condition flexible fuel vehicle in which there is a hardware malfunction. It is noted that the exemplary detected air-fuel ratio shown in FIG. 7(a) differs from that shown in FIG. 3; this difference is a result of the cold-start condition.

With reference to FIG. 7(a), a slope of a line 132a expressing the air-fuel ratio detected during the fuel mixing period 126 is, for the purposes of the herein described illustration, assumed to be that of a normally operating system 100 in which there is no hardware malfunction. The slope of line 132a therefore represents the expected slope of the method illustrated in FIG. 6. The slopes of lines 132b and 132c, which express the air-fuel ratio detected during the fuel mixing period 126 of FIGS. 7(b) and 7(c), respectively, differ substantially from the slope of line 132a of FIG. 7(a) (i.e, the expected slope). It is to be appreciated that though the change in the air-fuel ratio detected in FIGS. 7(b) and 7(c), i.e., the slope of the detected air-fuel ratio over fuel consumed, is different from that in FIG. 7(a), the flexible fuel is mixing according to a consistent and/or predictable rate in each of the three examples. As such, the slopes in FIGS. 7(a), 7(b), and 7(c) should be identical or substantially similar (i.e., within a threshold range), and the different slopes 132b, 132c shown in FIGS. 7(b) and 7(c) may be concluded to be the result of hardware malfunction.

For illustrative purposes, the slopes shown in FIGS. 7(b) and 7(c) are shown to greatly differ from that shown in FIG. 7(a). However, this need not be the case. To allow for more accurate determination of differences in the detected slope of the air-fuel ratio over fuel consumption and the expected slope of the air-fuel ratio over fuel consumption, the detected slope may be calculated as a numerical value and compared to a corresponding numerical value for the expected slope. To do so, a raw slope of the air-fuel ratio over consumed fuel may be used. Alternatively, a best-fit line may be applied to the air-fuel ratio over fuel consumption and a slope of the best-fit line may be calculated. Furthermore, the slope may be integrated and later compared to a criteria value. Returning to FIG. 6, when the slope difference is greater than or equal to a predetermined slope difference threshold value (S53: YES), the detecting unit 104 detects a hardware malfunction (S54). In this situation (i.e., S52: YES), the observed mixing of the flexible fuel introduced during the refuel event 130 with that previously in the vehicle fuel tank (i.e., the observed slope) differed from the expected mixing (i.e., the expected slope) by at least the predetermined slope difference threshold value. The slope difference threshold value is predetermined to be greater than an expected or normal variance from the expected slope, and therefore the slope difference being greater than the slope difference threshold value indicates the hardware has malfunctioned (S54).

However, when the slope difference is less than the predetermined slope difference threshold value (S53: No), it can be concluded that the hardware has not malfunctioned. Accordingly, the detecting unit 104 detects the air-fuel ratio using the air-fuel sensor 108 during the post-fuel mix period 128, and learns the ethanol concentration of the fully mixed flexible fuel based on the air-fuel ratio detected during the post-fuel mix period (S55).

It is to be appreciated the above-described method may vary while remaining in the scope of the present application. For example, the method shown in FIG. 2 may omit the steps S20 and S50 wherein the vehicle temperature is detected and compared to the vehicle temperature threshold value and the cold-start ethanol concentration and hardware malfunction determination is performed. Such processing would leave the primary ethanol concentration and hardware malfunction determination (S30) and the secondary ethanol concentration and hardware malfunction determination (S40). Furthermore, the method may include other or additional hardware malfunction detecting processing. For example, when the refuel event is not detected, any detected change in the air-fuel ratio may be determined as being due to a hardware malfunction.

It also to be appreciated that the flexible fuel need not be a mixture of gasoline and ethanol. The herein described system and method may be configured to determine the concentration of any component part or parts in any type of flexible fuel. Furthermore, the system and method may be configured to learn or determine flexible fuel properties other than or in addition to the ethanol (or different component part) concentration.

Furthermore, it is to be appreciated that insofar as the various components of the system 100 have been described as being integrated with and/or separate from one another, these components may be combined or separated in any suitable manner while remaining within the scope of the present application. Any and all of the described components of the system 100 may be provided as hardware elements and/or via a software-implemented control program saved in a memory which causes one or more processors to perform the herein described functions.

Lastly, it will be appreciated that various of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A method for determining a flexible fuel ethanol concentration and detecting a hardware malfunction, comprising:
   detecting whether a refuel event has occurred; and
   when occurrence of the refuel event is detected, performing a primary ethanol concentration and hardware malfunction determination, said primary ethanol concentration and hardware malfunction determination including:
      detecting an air-fuel ratio during a pre-fuel mix period and learning the air-fuel ratio detected during the pre-fuel mix period as a current hardware reference value, the pre-fuel mix period being a period during which only flexible fuel which has not mixed with flexible fuel from the refuel event is being consumed by a vehicle engine;
      determining a hardware reference value difference between the current hardware reference value and a previous hardware reference value from an immediately preceding vehicle driving cycle occurring prior to the refueling event;
      when said hardware reference value difference is greater than or equal to a predetermined hardware reference value threshold, detecting a hardware malfunction; and
      when said hardware reference value difference is less than the predetermined hardware reference value threshold, detecting the air-fuel ratio during a post-fuel mix period following the pre-fuel mix period and learning an ethanol concentration based on the air-fuel ratio detected during the post-fuel mix period.

2. The method according to claim 1, further comprising:
   when occurrence of the refuel event is not detected, performing a secondary ethanol concentration and hardware malfunction determination, the secondary ethanol concentration and hardware malfunction determination including:
      detecting the air-fuel ratio during the pre-fuel mix period and learning the air-fuel ratio detected during the pre-fuel mix period as the current hardware reference value, and detecting the air-fuel ratio during the post-fuel mix period and learning the air-fuel ratio detected during the post-fuel mix period as a comparative hardware reference value;
      determining a comparative hardware reference value difference between the current hardware reference value and the comparative hardware reference value;
      when the comparative hardware reference value difference is greater than or equal to a predetermined offset threshold value, learning the ethanol concentration based on the air-fuel ratio detected during the post-fuel mix period; and
      continuously detecting the air-fuel ratio during the post-fuel mix period and when the air-fuel ratio detected during the post-fuel mix period is detected to change by greater than a predetermined air-fuel malfunction threshold, detecting the hardware malfunction.

3. The method according to claim 2, wherein
   the post-fuel mix period is a period beginning when flexible fuel added during the refuel event has fully mixed with flexible fuel in a vehicle fuel tank prior to the refuel event, and during which fully mixed flexible fuel is being consumed by a vehicle engine,
   the fuel mixing period is a period between the pre-fuel mix period and the post-fuel mix period during which partially mixed flexible fuel is being consumed by the vehicle engine.

4. The method according to claim 1, wherein
   the post-fuel mix period is a period beginning when flexible fuel added during the refuel event has fully mixed with flexible fuel in a vehicle fuel tank prior to the refuel event, and during which fully mixed flexible fuel is being consumed by a vehicle engine.

5. The method according to claim 1, wherein detecting whether a refuel event has occurred includes:
   comparing a previous fuel level measured during the immediately preceding vehicle driving cycle with a current fuel level;
   when a difference between the previous fuel level and the current fuel level is greater than or equal to a predetermined fuel level difference, the occurrence of the refuel event is detected; and
   when the difference between the previous fuel level and the current fuel level is less than the predetermined fuel level difference, the occurrence of the refuel event is not detected.

6. The method according to claim 1, wherein the previous hardware reference value is learned as the air-fuel ratio detected at a conclusion of the immediately preceding vehicle driving cycle, the conclusion of the immediately preceding driving cycle being the turning off of the vehicle, and
   detecting the air-fuel ratio during the pre-fuel mix period and learning the air-fuel ratio detected during the pre-fuel mix period as the current hardware reference value takes place immediately following start-up of the vehicle.

7. The method of claim 1 further comprising:
   immediately following start-up of a vehicle, detecting whether a refuel event has occurred and detecting a vehicle temperature; and
   when the occurrence of the refuel event is detected and the vehicle temperature is detected to be less than a vehicle temperature threshold value, performing a cold-start ethanol concentration and hardware malfunction determination, said cold-start ethanol concentration and hardware malfunction determination including:
      continuously detecting an air-fuel ratio during a fuel mixing period following a pre-fuel mix period and prior to a post-fuel mix period, and calculating an observed slope of the air-fuel ratio detected during the fuel mixing period over an amount of fuel consumed during the fuel mixing period;
      determining a slope difference between the observed slope and a predetermined expected slope;
      when said slope difference is greater than or equal to a predetermined slope difference threshold value, detecting a hardware malfunction; and
      when said slope difference is less than the predetermined slope difference threshold value, detecting the air-fuel ratio during the post-fuel mix period and learning an ethanol concentration based on the air-fuel ratio detected during the post-fuel mix period.

8. The method according to claim 7, further comprising:
   when occurrence of the refuel event is detected and the vehicle temperature is detected to be greater than or equal to the vehicle temperature threshold value, performing a primary ethanol concentration and hardware malfunction determination, said primary ethanol concentration and hardware malfunction determination including:
- detecting the air-fuel ratio during the pre-fuel mix period and learning the air-fuel ratio detected during the pre-fuel mix period as a current hardware reference value;
- determining a hardware reference value difference between the current hardware reference value and a previous hardware reference value from an immediately preceding vehicle driving cycle occurring prior to the refueling event;
- when said hardware reference value difference is greater than or equal to a predetermined hardware reference value threshold, detecting the hardware malfunction; and
- when said hardware reference value difference is less than the predetermined hardware reference value threshold, detecting the air-fuel ratio during the post-fuel mix period and learning the ethanol concentration based on the air-fuel ratio detected during the post-fuel mix period.

9. The method according to claim 8, further comprising: when occurrence of the refuel event is not detected, performing a secondary ethanol concentration and hardware malfunction determination, the secondary ethanol concentration and hardware malfunction determination including:
- detecting the air-fuel ratio during the pre-fuel mix period and learning the air-fuel ratio detected during the pre-fuel mix period as the current hardware reference value, and detecting the air-fuel ratio during the post-fuel mix period and learning the air-fuel ratio detected during the post-fuel mix period as a comparative hardware reference value;
- determining a comparative hardware reference value difference between the current hardware reference value and the comparative hardware reference value;
- when the comparative hardware reference value difference is greater than or equal to a predetermined offset threshold value, learning the ethanol concentration based on the air-fuel ratio detected during the post-fuel mix period; and
- continuously detecting the air-fuel ratio during the post-fuel mix period and when the air-fuel ratio detected during the post-fuel mix period is detected to change by greater than a predetermined air-fuel malfunction threshold, detecting the hardware malfunction.

10. The method according to claim 8, wherein the previous hardware reference value is learned as the air-fuel ratio detected at a conclusion of the immediately preceding vehicle driving cycle.

11. The method according to claim 7, further comprising: when occurrence of the refuel event is not detected, performing a secondary ethanol concentration and hardware malfunction determination, the secondary ethanol concentration and hardware malfunction determination including:
- detecting the air-fuel ratio during the pre-fuel mix period and learning the air-fuel ratio detected during the pre-fuel mix period as the current hardware reference value, and detecting the air-fuel ratio during the post-fuel mix period and learning the air-fuel ratio detected during the post-fuel mix period as a comparative hardware reference value;
- determining a comparative hardware reference value difference between the current hardware reference value and the comparative hardware reference value;
- when the comparative hardware reference value difference is greater than or equal to a predetermined offset threshold, learning the ethanol concentration based on the air-fuel ratio detected during the post-fuel mix period; and
- continuously detecting the air-fuel ratio during the post-fuel mix period and when the air-fuel ratio detected during the post-fuel mix period is detected to change by greater than a predetermined air-fuel malfunction threshold, detecting the hardware malfunction.

12. The method according to claim 7, wherein
- the pre-fuel mix period is a period during which only flexible fuel in a vehicle fuel line immediately prior to start-up of the vehicle is being consumed by a vehicle engine,
- the post-fuel mix period is a period beginning when flexible fuel added during the refuel event has fully mixed with flexible fuel in a vehicle fuel tank prior to the refuel event, and during which fully mixed flexible fuel is being consumed by a vehicle engine,
- the fuel mixing period is a period between the pre-fuel mix period and the post-fuel mix period during which partially mixed flexible fuel is being consumed by the vehicle engine.

13. The method according to claim 7, wherein detecting whether a refuel event has occurred includes:
- comparing a previous fuel level measured at a conclusion of the immediately preceding vehicle driving cycle with a current fuel level measured immediately following start-up of the vehicle;
- when a difference between the previous fuel level and the current fuel level is greater than or equal to a predetermined fuel level difference, the occurrence of the refuel event is detected; and
- when the difference between the previous fuel level and the current fuel level is less than the predetermined fuel level difference, the occurrence of the refuel event is not detected.

14. The method according to claim 7, wherein the previous hardware reference value is learned as the air-fuel ratio detected at a conclusion of the immediately preceding vehicle driving cycle.

* * * * *